(12) United States Patent
He et al.

(10) Patent No.: US 6,718,008 B1
(45) Date of Patent: Apr. 6, 2004

(54) X-RAY DIFFRACTION SCREENING SYSTEM WITH RETRACTABLE X-RAY SHIELD

(75) Inventors: Bob Baoping He, Madison, WI (US); Frank Feng Jin, Fitchburg, WI (US)

(73) Assignee: Bruker AXS, Inc., Madison, WI (US)

( * ) Notice: Subject to any disclaimer, the term of this patent is extended or adjusted under 35 U.S.C. 154(b) by 0 days.

(21) Appl. No.: 10/127,352

(22) Filed: Apr. 22, 2002

(51) Int. Cl.[7] .............................................. G01N 23/20
(52) U.S. Cl. ........................................ 378/71; 378/206
(58) Field of Search ........................... 378/70, 71, 72, 378/73, 75, 76, 79, 81, 206

(56) References Cited

U.S. PATENT DOCUMENTS

| | | | | |
|---|---|---|---|---|
| 3,663,812 A | * | 5/1972 | Koenig et al. | 378/49 |
| 5,359,640 A | * | 10/1994 | Fink et al. | 378/79 |
| 6,371,640 B1 | * | 4/2002 | Hajduk et al. | 378/208 |
| 6,404,849 B1 | * | 6/2002 | Olson et al. | 378/79 |
| 6,459,763 B1 | * | 10/2002 | Koinuma et al. | 378/71 |
| 6,507,636 B1 | * | 1/2003 | Lehmann | 378/79 |
| 6,512,814 B2 | * | 1/2003 | Yokhin et al. | 378/82 |
| 6,535,575 B2 | * | 3/2003 | Yokhin | 378/82 |
| 6,577,705 B1 | * | 6/2003 | Chang et al. | 378/45 |

* cited by examiner

*Primary Examiner*—David V. Bruce
*Assistant Examiner*—Allen C. Ho
(74) *Attorney, Agent, or Firm*—Kudirka & Jobse, LLP

(57) ABSTRACT

An x-ray diffraction analysis system provides the automated x-ray diffraction analysis of a plurality of samples in a multiple-cell sample holder. The system includes x-ray source, a detector, a movable sample support and a retractable x-ray shield. The retractable shield is movable between a retracted position, in which optical positioning equipment may be used to locate each sample in the proper testing position, and an extended position, in which stray x-ray energy is blocked. The x-ray energy blocked by the shield includes x-rays diffracted from samples closer to the x-ray source than the sample under test, and x-rays from the source directed toward samples further from the source than the sample under test. Automated movement of the sample support and shield allows for an automated routine to sequentially position each sample, move the shield into the extended position and perform the desired analysis.

35 Claims, 4 Drawing Sheets

X-RAY DIFFRACTION SCREENING SYSTEM WITH RETRACTABLE X-RAY SHIELD

FIELD OF THE INVENTION

This invention relates generally to the field of x-ray diffraction analysis and, more particularly, to the use of reflection mode diffraction for combinatorial screening.

BACKGROUND OF THE INVENTION

Combinatorial chemistry refers generally to the testing of a large number of related materials and the storing of analytical data resulting from the tests. It is desirable in a number of analytical disciplines to perform rapid screening tests on tens, hundreds, or even thousands of related samples to evaluate variations of composition, structure and property. The results are then used to build a material library. X-ray diffraction is a useful technique for performing sample analysis because extensive information may be acquired from the diffraction pattern, and the testing is fast and non-destructive. However, many combinatorial chemistry applications, such as the analysis of certain pharmaceutical materials, require x-ray diffraction screening in a low Bragg angle range.

In low angle diffraction measurement, the incident x-ray beam is spread out over the sample surface in an area much larger than the cross-sectional size of the original x-ray beam. This becomes a problem in combinatorial chemistry applications because it is desirable to use a two-dimensional sample tray having many sample cells that lie adjacent to each other. Because the sample cells are close to each other, the spread beam may cause cross contamination in the collected diffraction data. That is, diffracted x-ray energy from a sample not under test could accidentally be detected by the detector, thereby affecting the results of the analysis of the sample under test. Conventionally, a shield (sometimes referred to as a "knife-edge") has been used to block, from reaching the detector, diffracted x-ray energy from all but the directions associated with the sample under test. This shield helps to improve the signal-to-noise ratio of the detected signal.

SUMMARY OF THE INVENTION

Although the shield is useful in blocking stray x-ray energy from samples surrounding a sample under test, it also acts as an obstruction to a view of the sample tray. In the present invention, a retractable shield is used that may be located in proper position to block stray x-ray energy during a test, but is then retracted while the sample tray is repositioned. This retraction of the shield allows a clear view of the sample tray. This, in turn, facilitates the use of a laser and video camera system used for automated alignment of the sample tray.

In accordance with the invention, an x-ray diffraction analysis apparatus performs an analysis on a plurality of samples in a multiple-cell sample holder. The apparatus includes a sample support upon which the sample holder may be located. Preferably, the sample support is automatically controlled to allow positioning of the sample for either fine-tuning for the sample testing itself, or for moving a new sample into testing position. When properly positioned, the sample under test undergoes x-ray diffraction analysis. An x-ray source is provided that directs x-ray radiation toward the sample under test, and x-ray radiation diffracted from the sample is detected by an x-ray detector.

In order to prevent x-ray radiation other than that diffracted from the a sample under test from reaching the detector, the retractable x-ray shield is placed in an extended position adjacent to the sample. The x-ray shield is movable between the extended position and a retracted position in which it is outside the field of view of an observation apparatus. Typically, such apparatus is positioned directly above the sample holder although, in general, the unobstructed view is from a position substantially along an axis perpendicular to the plane of the sample holder that intersects the center of the sample. If the sample holder is held in a horizontal plane, this means an unobstructed view of the sample from directly above it. The observation system may be a video camera/microscope combination used with a laser light source. Such an observation system can be used to precisely position a desired one of the samples relative to the testing apparatus.

Some of the desirable features of the shield include a tapering toward the sample so that a "knife-edge" is the closest part of the shield to the sample. The positioning of the shield in the extended position is such that it blocks diffracted x-ray energy from samples closer to the x-ray source than the sample under test, and it blocks x-ray energy from the x-ray source that is directed toward a sample further from the x-ray source than the first sample. A particularly suitable gap distance between the surface of the sample and the knife-edge may be determined from other parameters of the system. Such a distance may be equal to the height of a triangle having a base of length S, where S is the distance between the centers of samples adjacent to each other along the primary dimension separating the x-ray source and the detector. The two sides of the triangle have respective angles (relative to the base) of $\theta_1$ and $\theta_2$, where $\theta_1$ is the angle between the primary emitting direction of the x-ray source and the surface of the sample holder, and $\theta_2$ is the angle between the primary detection direction of the detector and the surface of the sample holder. The height of the triangle is the distance from the base to the point at which these two sides intersect.

Like the sample support, the shield also preferably includes an actuator by which it may be automatically moved. This allows the system to perform automatic testing of some or all of the samples of the sample holder. The sample holder would be positioned on the sample support with a first sample roughly aligned at a testing position. The positioning of the first sample would then be examined using the observation apparatus. Using the laser to illuminate the sample surface, the output from the video camera would provide feedback for a fine-tuning of the sample position by movement of the sample support with the sample position adjuster. This positioning is done with the shield in the retracted position. Once the positioning step is complete, the actuator for the shield is activated to move it into the extended position. The x-ray source and detector are then activated, and the diffracted x-rays from the sample under test are detected and the diffraction data recorded. The actuator then moves the shield to the retracted position, and the next sample to be tested is moved into the testing position. The steps of positioning and testing are then repeated for the new sample and for each sample after that until the final sample is reached. Once the system determines that the final sample has been reached, testing routine halts.

BRIEF DESCRIPTION OF THE DRAWINGS

The above and further advantages of the invention may be better understood by referring to the following description in conjunction with the accompanying drawings in which.

DETAILED DESCRIPTION

Figure 1:
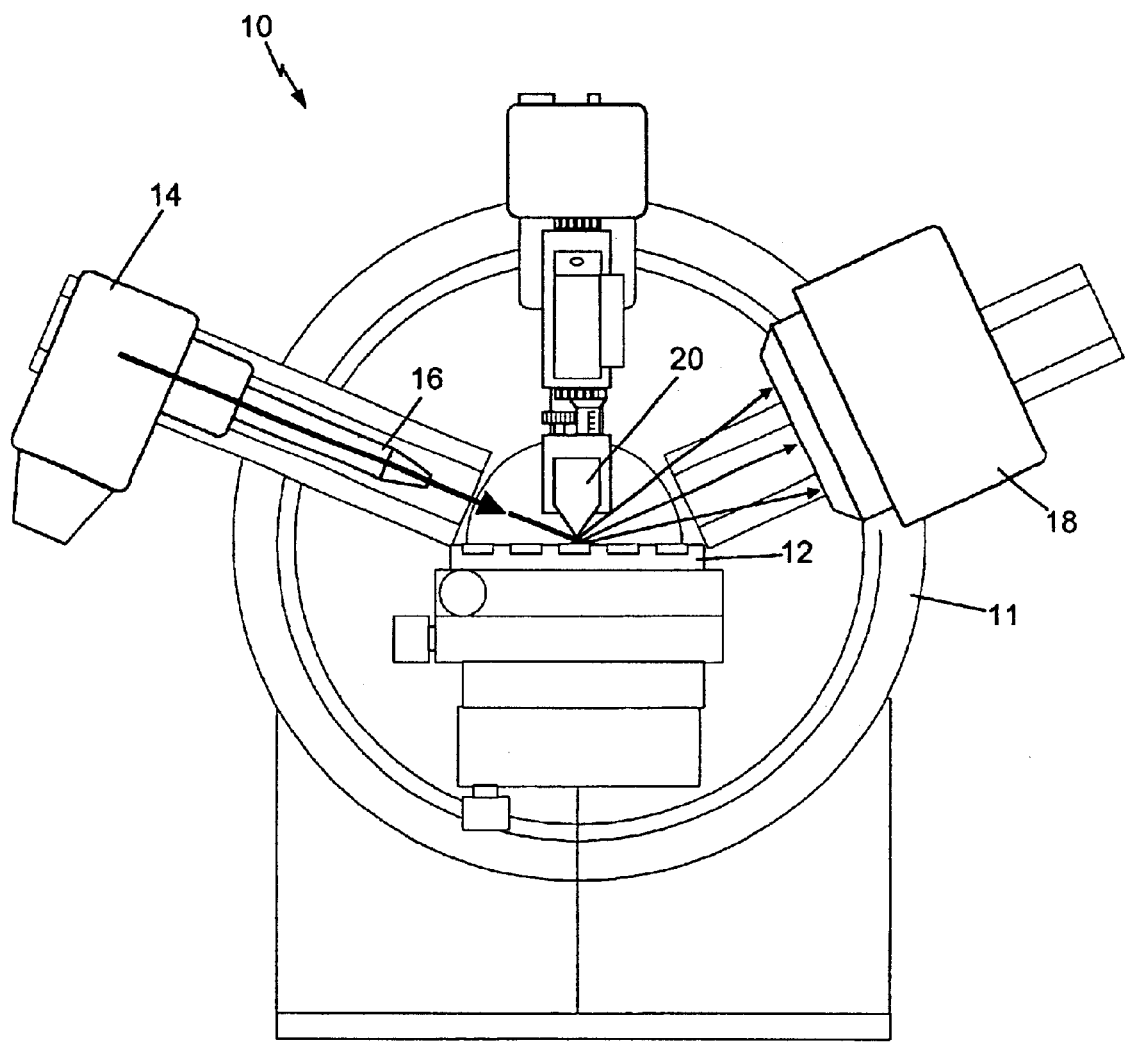
FIG. 1 is a schematic front view of an x-ray diffraction analysis system according to the present invention.

FIG. 1 is a schematic front view of an x-ray diffraction combinatorial screening system 10 according to the present invention. Different samples to be tested are located in separate sample cells of sample tray 12. The sample tray is positioned such that one of the sample cells can be examined at any given time. The diffraction analysis makes use of an x-ray source 14 from which an x-ray beam is emitted. The x-ray source 14, along with other components of the system, are mounted to a goniometer 11. The x-ray beam, the direction of which is indicated by an arrow in the figure, passes through collimator 16, and is incident upon the sample material under test. Upon encountering the sample under test, the x-ray beam is diffracted by the sample at a low angle toward two-dimensional detector 18.

Located above the sample under test is x-ray shield 20, which serves to block x-ray radiation not diffracted from the sample under test. The shield is tapered toward the sample, taking the form of a "knife-edge" in the vicinity of the sample. The shield 20 is connected to an actuator that moves the shield between an extended position and a retracted position. In the extended position, as shown in FIG. 1, the shield 20 is in close proximity to the sample, blocking a number of different directions from which stray x-ray energy could be directed toward the detector 18. When in the retracted position, however, the shield is much further from the sample under test, allowing inspection for positioning and other purposes.

Figure 2:
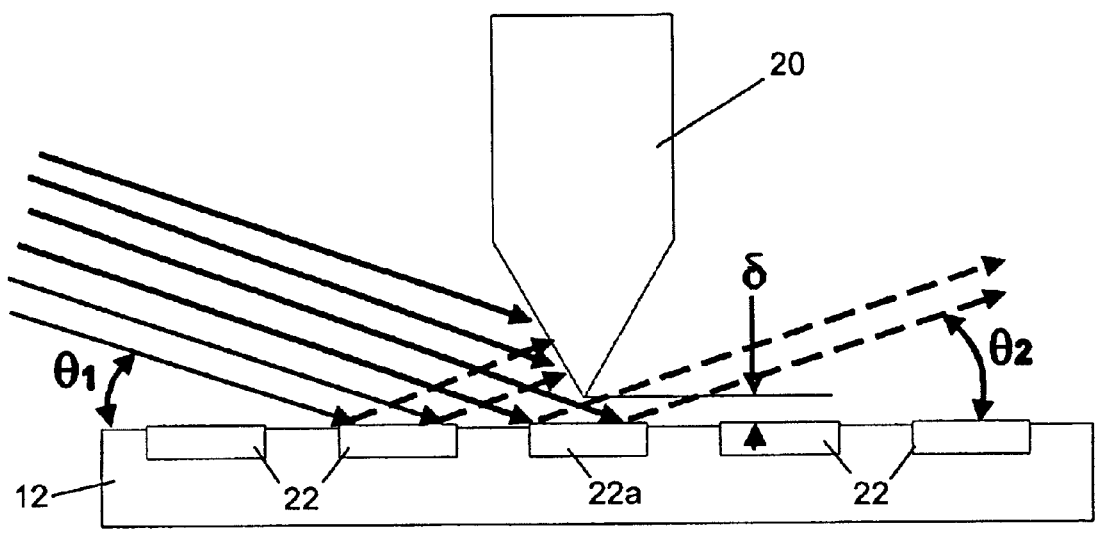
FIG. 2 is a schematic close-up front view of a sample holder and an x-ray shield of the system of FIG. 1.

FIG. 2 is a schematic, cross-sectional view of the shield 20 in the extended position adjacent to the sample tray 12. In this view, only one row of sample cells 22 is visible, although those skilled in the art will understand that the sample tray will often have a two-dimensional array of sample cells 22. In the extended position shown, the shield 20 is closest to sample cell 22a, and provides shielding while the sample in this cell is under test. In order to minimize any diffracted x-ray energy from adjacent sample cells reaching the sample detector, the extended position of the shield blocks both original and diffracted x-ray energy. In the figure, the original x-ray energy from the source is depicted by solid line arrows, while diffracted x-ray energy is depicted by broken line arrows. As shown, the shield is close enough to the sample cell 22a that original x-ray energy is blocked that might otherwise be incident on sample cells to the side of the shield 22 away from the x-ray source. Similarly, x-ray energy to the on the side of the shield closer to the x-ray source may have some original x-ray energy incident upon them. However, the shield is close enough to the sample tray 12 that the resulting energy diffracted from these cells is also blocked by the shield 22, and does not reach the detector.

Figure 3:
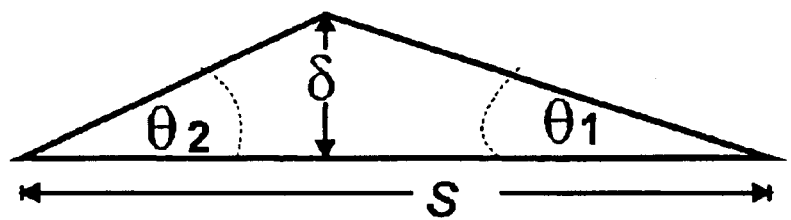
FIG. 3 is a graphical depiction of a technique for determining a proper distance between a sample and the shield of the system of FIG. 1 when the shield is in an extended position.

As shown in FIG. 2, the knife-edge of the shield 20 is separated from the top surface of the samples 12 by a gap $\delta$. For a given application, the proper size of this gap may be determined by the dimensions of the sample tray and the angles of incidence ($\theta_1$) and refraction ($\theta_2$) during the experiment. Shown in FIG. 3 is a graphical representation of the triangular relationship between these parameters. For a given distance S between sample cell centers in the direction perpendicular to the knife-edge of the shield, the appropriate gap $\delta$ may be found from the triangular model of FIG. 3. With a base of distance S, the two remaining sides of the triangle extend from opposite ends of the triangle at respective angles relative to the base of $\theta_1$ and $\theta_2$. The distance between the intersection of these two sides and the base gives the appropriate gap distance $\delta$.

Figure 4:
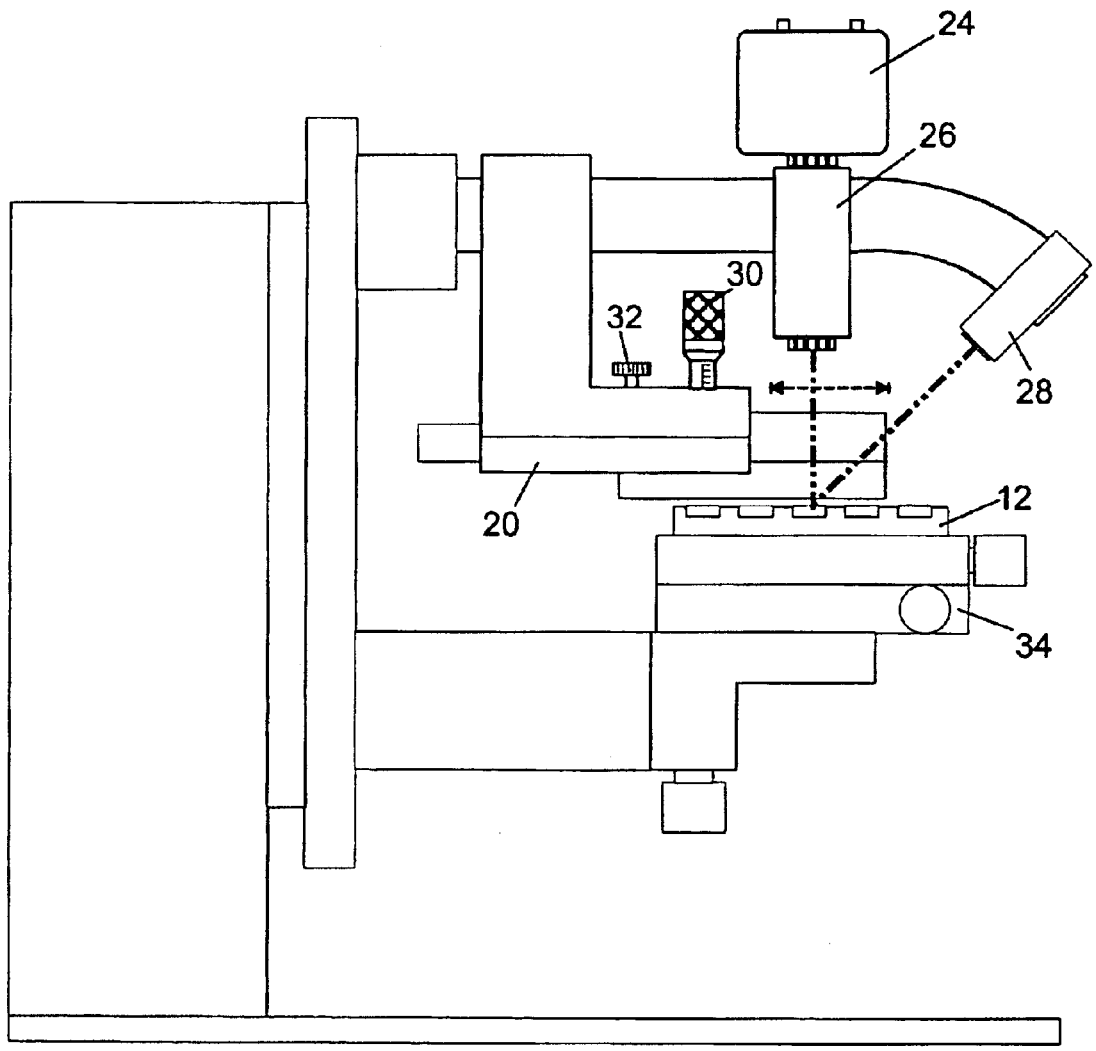
FIG. 4 is a schematic side view of the system of FIG. 1 showing the different positions of the x-ray shield.

Operation of a system according to the present invention may be better understood from FIG. 4, which is a schematic side view. The solid line image of the shield 20 is shown in the retracted position, while the shield portion is also shown in broken lines in the extended position (the remaining portion of the shield assembly is shown the retracted position but, for purposes of clarity, no broken line rendering of this portion is shown). Also shown in the figure is video camera 24, which uses a microscope 26 to focus on the sample cell in position to be tested. As shown, if the shield were in the extended position, the video camera would be obstructed from viewing the entire sample cell. However, with the shield 20 in the retracted position, there is no such obstruction. A laser 28 is used to illuminate the sample surface, allowing the video camera to detect the sample for positioning purposes. A system that uses a laser and video camera in this way for sample positioning is disclosed in U.S. Pat. No. 5,359,640, which is incorporated herein by reference.

Certain fine tuning adjustment mechanisms for the shield are also shown in FIG. 2. A micrometer 30 may be used to make adjustments in the gap size $\delta$ by moving the entire knife-edge portion up and down by incremental amounts. An angular adjustment 32 is also provided that may be used to adjust the horizontal angle of the knife-edge, to ensure that it is parallel to the surface of the sample tray. FIG. 4 also shows the sample support 34, which is conventional in the art, and may be used to adjust the sample position in three dimensions.

Figure 5:
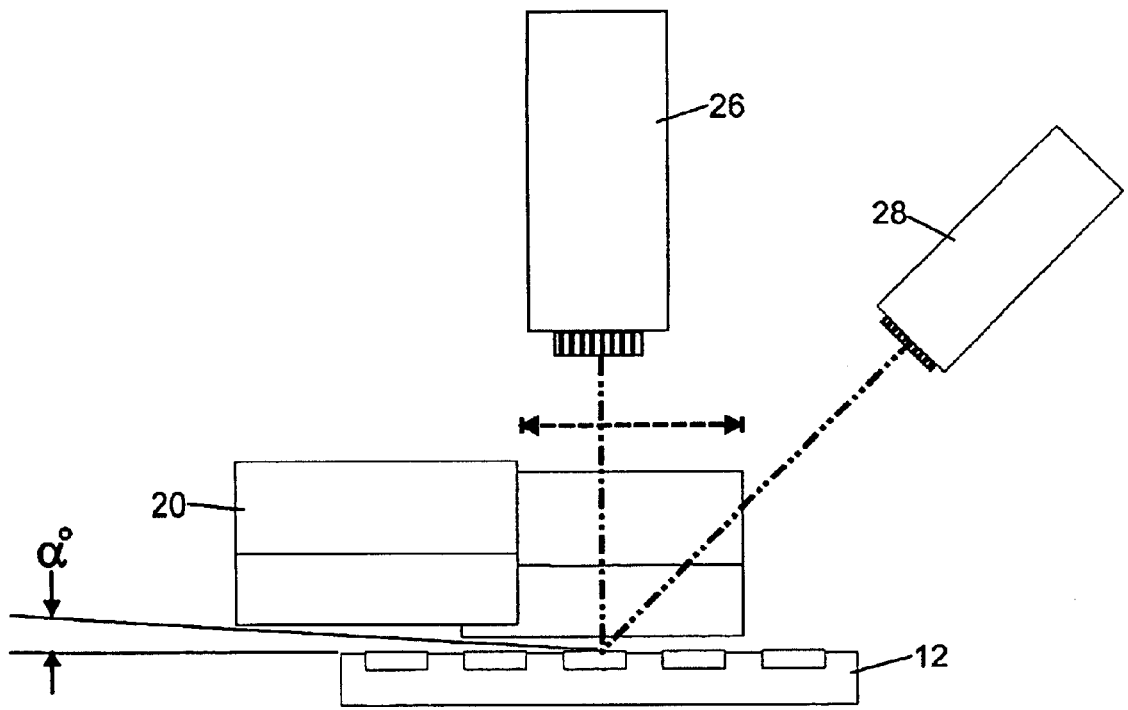
FIG. 5 is a schematic close-up side view of the system of FIG. 1 showing the different positions of the shield relative to the optical observation equipment of the system.

FIG. 5 is an enlarged schematic side view showing the retracted and extended positions of the knife-edge portion of the shield. Again, the extended position is indicated by broken lines, while the retracted position is indicated by solid lines. The beam from the laser 28 and the optical axis of the microscope 26 intersect at the "instrument center." With the video camera receiving an image from the microscope, the sample position can be determined by the laser spot position on the sample image. The sample height may then be automatically adjusted to place the surface of the sample at the instrument center. During this positioning step, the shield is in the retracted position, out of the way of the video positioning equipment. Once the sample is in position, the shield is moved into the extended position adjacent to the sample, the x-ray diffraction testing begins. As shown in FIG. 5, the shield 22 20 is moved far enough out of the field of the microscope 28 as to not interfere with video information collection. The shield may also be given a take off angle a, which may help to reduce the risk of contact between the shield and adjacent regions of the sample tray 12.

Figure 6:
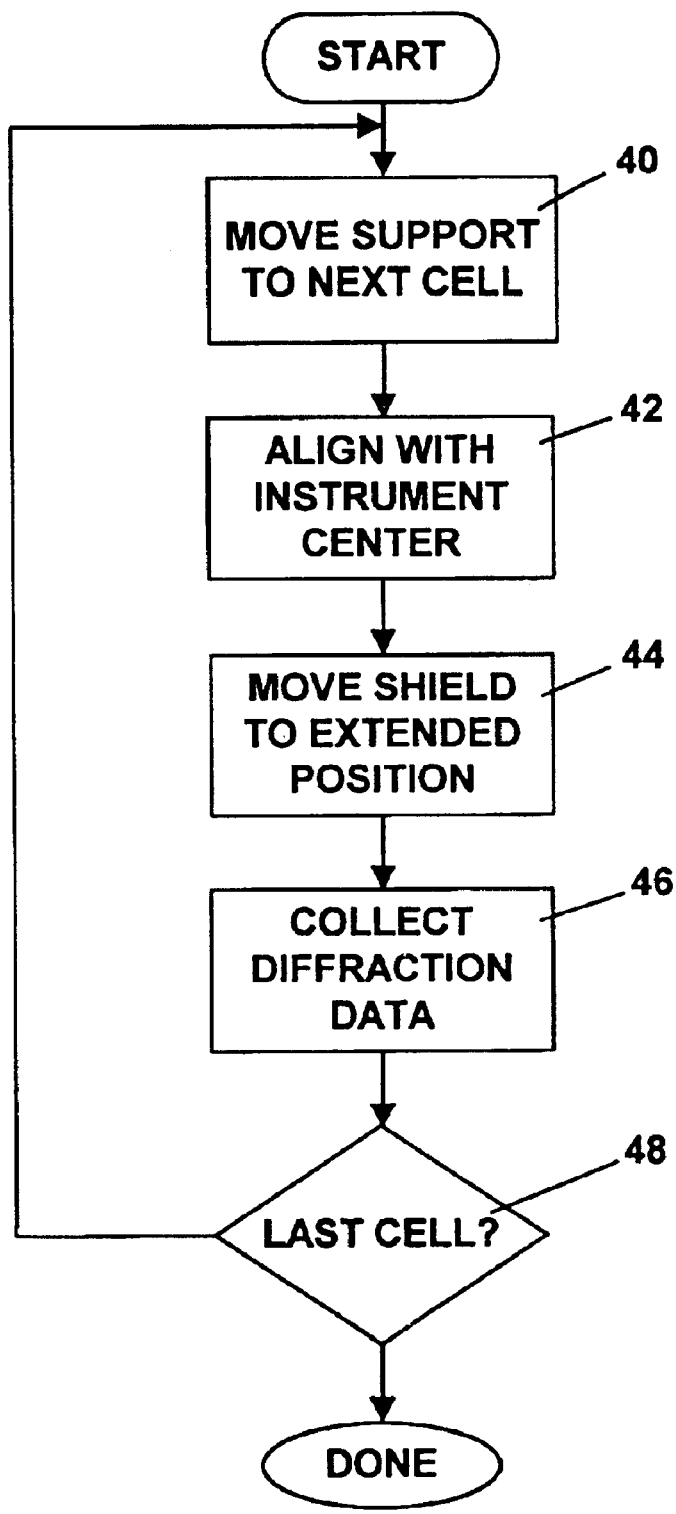
FIG. 6 is a flowchart depicting a possible sample testing routine for use with the system of FIG. 1.

The testing of each sample in the sample tray 12 may be done automatically, and used, for example, for combinatorial screening. With the sample tray 12 in a starting position, a user could first adjust the angle of the shield relative to the new sample tray using the angular adjustment 32. A first sample cell 22 could then be aligned using the laser video system, after which the gap between the sample and the knife-edge of the shield could be adjusted with micrometer 30. An automated screening routine could then be run with a central control system. Such a routine might follow the steps described below, and depicted in FIG. 6.

The sample positioning apparatus is first adjusted to position a cell to be examined near the instrument center (step 40). Using the laser/video system, the cell is then be more closely aligned with the instrument center (step 42). Once in position, the shield 20 is extended (step 44), and the diffraction data is collected (step 46). The system then determines whether the cell that was just examined is the last cell (step 48) and, if not, the routine returns to step 40. If it is the last cell, the procedure halts. Software routines necessary to implement such are routine are well within the ability of those skilled in the art, and are not described in any further detail herein.

While the invention has been shown and described with reference to a preferred embodiment thereof, those skilled in the art will recognize that various changes in form and detail may be made herein without departing from the spirit and scope of the invention as defined by the appended claims.

What is claimed is:

1. An x-ray diffraction analysis apparatus for performing x-ray diffraction analysis on a plurality of samples in a multiple-cell sample holder, the system comprising:
   a sample support upon which the sample holder is located;
   an x-ray source that directs x-ray radiation toward a first one of the cells of the sample holder;
   an x-ray detector that detects x-ray energy diffracted from sample material of the first sample cell; and
   a retractable x-ray shield that may be moved between an extended position, in which it is located so as to block x-ray energy from the source from reaching the detector except that x-ray energy diffracted from the first sample, and a retracted position in which it is further from the sample so as to allow an improved field of view of the first sample than is available when it is in the extended position.

2. An apparatus according to claim 1 wherein the sample support is movable in the two dimensions parallel to the plane of the sample holder.

3. An apparatus according to claim 2 wherein the sample support is movable in the direction perpendicular to the plane of the sample holder.

4. An apparatus according to claim 1 wherein the shield includes a region that tapers to a knife-edge in the vicinity of the first sample.

5. An apparatus according to claim 1 wherein, in the extended position, the shield blocks diffracted x-ray energy from a sample closer to the x-ray source than the first sample.

6. An apparatus according to claim 1 wherein, in the extended position, the shield blocks x-ray energy from the x-ray source that is directed toward a sample further from the x-ray source than the first sample.

7. An apparatus according to claim 1 wherein, in the extended position, the shield is separated from the first sample by a distance δ, and δ is approximately equal to the height of a triangle having a base of length S and two sides with respective angles relative to the base of $\theta_1$ and $\theta_2$, S being equal to the distance between the centers of samples adjacent to one another along the primary dimension separating the x-ray source and the detector, $\theta_1$ being the angle between the primary emitting direction of the x-ray source and the surface of the sample holder, and $\theta_2$ being the angle between the primary detection direction of the detector and the surface of the sample holder.

8. An apparatus according to claim 1 further comprising an optical observation apparatus that optically detects the position of the first sample and may be used for adjusting the position of the sample holder.

9. An apparatus according to claim 8 wherein the observation apparatus comprises a video camera.

10. An apparatus according to claim 9 wherein the observation apparatus comprises a microscope.

11. An apparatus according to claim 8 wherein the observation apparatus comprises a laser focused on the first sample.

12. An apparatus according to claim 8 wherein the apparatus further comprises a sample position adjuster that moves the sample support in response to positioning data collected by the observation apparatus.

13. An apparatus according to claim 12 wherein the sample position adjuster moves the sample support to properly position the first sample for diffraction analysis.

14. An apparatus according to claim 12 wherein the sample position adjuster moves the sample support to move a new sample into position for diffraction analysis in place of the first sample.

15. An apparatus according to claim 8 wherein the shield obstructs a field of view of the observation apparatus in the extended position.

16. An apparatus according to claim 15 further comprising a shield actuator that moves the shield from the extended position to the retracted position to allow positioning of the sample support using positioning information collected by the observation apparatus.

17. An apparatus according to claim 1 wherein the shield, in the retracted position, is further from the sample holder than when in the extended position.

18. An apparatus according to claim 1 wherein the shield includes a fine tuning adjustment that allows adjustment of its position relative to the sample support when in the extended position.

19. An x-ray diffraction analysis apparatus for performing x-ray diffraction analysis on a plurality of samples in a multiple-cell sample holder, the system comprising:
   a movable sample support upon which the sample holder is located;
   an x-ray source that directs x-ray radiation toward a first one of the cells of the sample holder;
   an x-ray detector that detects x-ray energy diffracted from sample material of the first sample cell;
   a retractable x-ray shield that may be moved between an extended position, in which it is located so as to block substantially all x-ray energy from the source from reaching the detector except that x-ray energy diffracted from the first sample, and a retracted position in which it is far enough from the sample as to be outside a field of view of the first sample from a position substantially along an axis perpendicular to the plane of the sample holder that intersects the center of the sample, wherein, in the extended position, the shield blocks diffracted x-ray energy from a sample closer to the x-ray source than the first sample and blocks x-ray energy from the x-ray source that is directed toward a sample further from the x-ray source than the first sample; and an optical observation apparatus the field of view of which is obstructed by the shield when in the extended position, but that optically collects information regarding the position of the first sample when the shield is in the retracted position that may be used for adjusting the position of the sample holder.

20. An apparatus according to claim 19 further comprising apparatus for the automated testing of sequential samples and the movement of the sample support to facilitate such testing, including a sample position adjuster that moves the sample support in response to positioning data collected by the observation apparatus to fine tune the positioning of the sample and to move a new sample into position in place of the first sample, and an actuator that moves the shield between the extended position and the retracted position.

21. A method for performing x-ray diffraction analysis on a plurality of samples in a multiple-cell sample holder, the method comprising:
locating a sample holder containing a plurality of samples on a sample support;
directing x-ray radiation toward a first one of the cells of the sample holder with an x-ray source;
detecting x-ray energy diffracted from sample material of the first sample cell with an x-ray detector; and
blocking extraneous x-ray energy from reaching the detector with a retractable x-ray shield that may be moved between an extended position, in which it is located so as to block substantially all x-ray energy from the source from reaching the detector except that x-ray energy diffracted from the first sample, but in which the shield at least partially obstructs a field of view of the first sample, and a retracted position in which said field of view is substantially unobstructed.

22. A method according to claim 21 wherein the sample support is movable in the three dimensions.

23. A method according to a claim 21 wherein the shield includes a region that tapers to a knife-edge in the vicinity of the first sample.

24. A method according to claim 21 wherein, in the extended position, the shield blocks diffracted x-ray energy from a sample closer to the x-ray source than the first sample as well as x-ray energy from the x-ray source that is directed toward a sample further from the x-ray source than the first sample.

25. A method according to claim 21 wherein, in the extended position, the shield is separated from the first sample by a distance δ, and δ is approximately equal to the height of a triangle having a base of length S and two sides with respective angles relative to the base of $\theta_1$ and $\theta_2$, S being equal to the distance between the centers of samples adjacent to one another along the primary dimension separating the x-ray source and the detector, $\theta_1$ being the angle between the primary emitting direction of the x-ray source and the surface of the sample holder, and $\theta_2$ being the angle between the primary detection direction of the detector and the surface of the sample holder.

26. A method according to claim 21 further comprising optically detecting the position of the first sample with an optical observation apparatus and using the optically detected information to adjust the position of the sample holder.

27. A method according to claim 26 wherein the observation apparatus comprises a video camera.

28. A method according to claim 27 wherein the observation apparatus comprises a microscope.

29. A method according to claim 26 wherein the observation apparatus comprises a laser focused on the first sample.

30. A method according to claim 26 wherein further comprising automatically adjusting the position of the sample holder with a sample position adjuster that moves the sample support in response to positioning data collected by the observation apparatus.

31. A method according to claim 26 wherein in the extended position the shield obstructs the viewing of the first sample with the observation apparatus, and wherein the method further comprises automatically moving the shield from the extended position to the retracted position with a shield actuator to allow positioning of the sample support using positioning information collected by the observation apparatus.

32. A method for performing x-ray diffraction analysis on a plurality of samples in a multiple-cell sample holder, the method comprising:
locating the sample holder on a movable sample support with a cell containing a sample under test positioned at a testing location;
observing the position of the sample under test with an optical observation apparatus;
adjusting the position of the sample under test with a sample position adjuster that moves the movable sample support in response to a signal from the observation apparatus;
moving a retractable x-ray shield from a retracted position, in which it does not significantly obstruct a view of the sample under test by the observation apparatus, to an extended position adjacent the sample under test in which it blocks substantially all x-ray energy from the source from reaching the detector except x-ray energy diffracted from the sample under test;
directing x-ray radiation toward a first one of the cells of the sample holder with an x-ray source and detecting x-ray energy diffracted from the sample under test with an x-ray detector, and
determining whether the sample under test is the last sample to be tested and, if not, adjusting the position of the sample holder to position a new sample to be tested at the testing location.

33. A method according to claim 32 wherein observing the position of the sample under test with an optical observation apparatus comprises observing the sample with an observation apparatus including a laser, a video camera and a microscope.

34. A method according to claim 32 wherein the method continues until each of the samples of the sample holder has been tested.

35. An x-ray shielding apparatus for blocking stray x-ray energy in an x-ray diffraction screening system including an x-ray source, an x-ray detector and a multi-cell sample holder in which a plurality of samples are contained, the apparatus comprising a movable shield that may be moved between an extended position, in which it is located so as to block x-ray energy from the source from reaching the detector, except that x-ray energy diffracted from a first sample of the sample holder, and a retracted position in which it is further from the sample holder so as to provide an improved field of view of the first sample than is available when it is in the extended position.

* * * * *